(12) United States Patent
Bashour

(10) Patent No.: US 12,733,790 B2
(45) Date of Patent: Sep. 15, 2026

(54) BALLOON ASSISTED CONTAINMENT OF INSUFFLATED ROBOTIC/ENDOSCOPIC OPERATIVE FIELD

(71) Applicant: Fadi N. Bashour, Westlake, OH (US)

(72) Inventor: Fadi N. Bashour, Westlake, OH (US)

(73) Assignee: Bashour Family Innovations, LLC, Westlake, OH (US)

( * ) Notice: Subject to any disclaimer, the term of this patent is extended or adjusted under 35 U.S.C. 154(b) by 404 days.

(21) Appl. No.: 18/532,198

(22) Filed: Dec. 7, 2023

(65) Prior Publication Data

US 2025/0185889 A1 Jun. 12, 2025

(51) Int. Cl.

| | |
|---|---|
| ***A61B 1/00*** | (2006.01) |
| ***A61B 1/015*** | (2006.01) |
| ***A61B 1/31*** | (2006.01) |
| ***A61M 13/00*** | (2006.01) |

(52) U.S. Cl.

CPC .......... *A61B 1/00082* (2013.01); *A61B 1/015* (2013.01); *A61B 1/31* (2013.01); *A61M 13/003* (2013.01)

(58) Field of Classification Search

CPC ....... A61B 1/00082; A61B 1/015; A61B 1/31; A61B 1/00135; A61B 1/018; A61M 13/003

See application file for complete search history.

(56) References Cited

U.S. PATENT DOCUMENTS

| | | | | |
|---|---|---|---|---|
| 4,295,464 | A * | 10/1981 | Shihata | A61M 25/1011 604/908 |
| 4,299,226 | A * | 11/1981 | Banka | A61M 25/0026 604/509 |
| 4,957,486 | A * | 9/1990 | Davis | A61M 25/01 600/116 |
| 5,908,445 | A * | 6/1999 | Whayne | A61B 1/0016 607/122 |
| 10,827,909 | B2 | 11/2020 | Bashour | |
| 11,179,027 | B2 | 11/2021 | Rentschler et al. | |
| 11,553,830 | B1 | 1/2023 | Farhadi | |

* cited by examiner

*Primary Examiner* — Theodore J Stigell

(74) *Attorney, Agent, or Firm* — Emerson, Thomson & Bennett, LLC; Roger D. Emerson; Peter R. Detorre

(57) ABSTRACT

A multi-working channel device with a cylindrical assembly having a distal end, a proximal end, an interior space, and an aperture. The multi-working channel device also has a longitudinally extending tube with a proximal end, a distal end that is coterminous with the distal end of the cylindrical assembly, and a balloon. The multi-working channel device also utilizes a stylet having a proximal end and a distal end that is connected to the balloon. The stylet can be adjusted between a home position and an active position. In the home position, the balloon is at least partially within the longitudinally extending tube. Alternatively, the active position deploys the balloon from the longitudinally extending tube. The stylet selectively urges the balloon to the active position, facilitating employment of the alimentary engagement device. In addition, the balloon is selectively inflated through the longitudinally extending tube.

20 Claims, 9 Drawing Sheets

36
10
30

40
42

36
30

40
42

BALLOON ASSISTED CONTAINMENT OF INSUFFLATED ROBOTIC/ENDOSCOPIC OPERATIVE FIELD

CROSS-REFERENCE TO RELATED APPLICATIONS

Not applicable.

STATEMENT REGARDING FEDERALLY SPONSORED RESEARCH AND DEVELOPMENT

Not applicable.

THE NAMES OF THE PARTIES TO A JOINT RESEARCH AGREEMENT

Not applicable.

STATEMENT REGARDING PRIOR DISCLOSURES BY THE INVENTOR OR A JOINT INVENTOR

Not applicable.

BACKGROUND OF THE INVENTION

The present disclosure relates to devices used in endoscopic surgeries. More particularly, it pertains to devices used in endoscopic and robotic surgeries.

Colorectal cancer is one of the top five most common diagnosed cancers in the United States. It is estimated that about three percent of the population has a lifetime risk of developing this type of cancer.

To combat this deadly statistic, colorectal cancer screening and endoscopic surgery help decrease mortality. For screening, an alimentary engagement device can be used. Examples include endoscopes or colonoscopes. These devices are long, slender medical instruments useful for examining the interior of hallow organs, such as the stomach and colon. These devices can have multiple channels and lenses to relay an image inside the hallow organ for examination by a physician or surgeon.

Additionally, a colonoscopy is a procedure helpful in identifying colorectal cancer or its precursors. During this procedure, a gastroenterologist examines the large intestine-colloquially known as the colon. The procedure screens for and detects polyps and tumors. In addition, this procedure helps in diagnosis of underlying conditions associated with changes in bowel habits, abdominal pain, unexplained weight loss, iron deficiency, and bleeding.

Following colonoscopies, patients may also require endoscopic colon surgery. During this procedure, insufflation (i.e., introduction of air) improves visualization of the interior of the alimentary canal. However, insufflation can also create abdominal discomfort and bloating for patients.

Another procedure is an endoscopic mucosal resection, where physicians and surgeons excise pre-cancerous and cancerous tumors, which stops these growths from becoming more deadly. However, during surgery, a patient may experience bleeding and perforation (i.e., a cut or a tear) of the colon, which allows air and other intestinal material to leak into the abdominal cavity. Such an event increases sepsis risk.

To attain focused insufflation, improvements have been attempted to limit the insufflation to the part of the alimentary canal undergoing examination or surgery. Examples include U.S. Pat. Nos. 11,179,027; 11,553,830. These designs include balloons that allow a user or skilled artisan to remotely inflate and manipulate the balloon while it is inside a patient.

However, shortcomings of these designs include the lack of adequate manipulation apart from either the endoscope or the catheter responsible for inflating the balloon. Lack of controlled placement and manipulation of the balloon is not ideal during use of an alimentary engagement device because the device or a catheter may not provide enough control to effectively place the balloon where originally intended or, alternatively, where needed following more complete examination once surgery has commenced.

Thus, the ongoing need for a device that allows for strategic placement—beyond utilization of the alimentary engagement device or balloon catheter—of a balloon during surgery. Such a solution increases the skilled artisan's ability to direct placement and deployment of an alimentary-canal balloon.

BRIEF SUMMARY OF THE INVENTION

Provided in this disclosure is a device utilizing balloon assisted containment of insufflated robotic/endoscopic operative fields. The device is a multi-working channel device able to meet the functional needs of physicians, surgeons, and other skilled artisans; specifically, the device meets the long-felt need: placing a balloon with greater precision than that provided via an endoscope or a balloon catheter. In one illustrative setting, the need for this increased level of precision may not be apparent until endoscopic colon surgery has already begun.

According to one aspect of the disclosure, this multi-working channel device has a cylindrical assembly. The skilled artisan would understand that the top of the cylindrical assembly could also be circular, beveled, or any other rounded shape. In addition, the cylindrical assembly could be made from plastic, polymeric material, or any other material deemed suitable by a skilled artisan.

According to one aspect of the disclosure, the cylindrical assembly has a distal end, a proximal end, an interior space, and an aperture. The aperture could be an opening, a hole, a gap, or any other break used by a skilled artisan. The skilled artisan would also understand that the aperture could be multiple sizes.

According to another aspect of the disclosure, the cylindrical assembly would have a channel. Exemplary embodiments include a main channel or a side channel. In yet another exemplary embodiment, the cylindrical assembly would have either a plurality of side channels, a combination of a main channel with a side channel, a combination of a main channel with a plurality of side channels, a side channel with one or more smaller side channels nested inside, or any other configuration of channels used by the skilled artisan. The skilled artisan would realize the channels require sufficient size, allowing utilization of surgical instruments. In addition, any channel could be covered by a flap. The flap may cover all or a portion of the channel. The skilled artisan would understand the flap to be movable such that a surgical instrument or other implement could pass through the flap. The skilled artisan would further understand that the flap could be made of a polymer, plastic, or any other material used by the skilled artisan.

In the exemplary cylindrical assembly embodiments having a main channel, the main channel would be disposed on one side of the interior space, while the side channels could be disposed on the opposite side of the interior space of the cylindrical assembly. In addition, the channels would be configured in a way enabling the skilled artisan to perform surgery.

According to another aspect of the disclosure, the multi-working channel device has a longitudinally extending tube with a proximal end, a distal end, and a balloon. The skilled artisan would appreciate that the longitudinally extending tube may be any length for use during a endoscopic colon surgery. The longitudinally extending tube could be made of rubber, plastic, polymeric material, a combination thereof, or any other material used by a skilled artisan.

An exemplary embodiment of the longitudinally extending tube would additionally comprise an auxiliary tube, wherein a balloon filling port is located outside of a patient's body. The skilled artisan would understand that the auxiliary tube could be made of rubber, plastic, polymeric material, or any other material used by the skilled artisan. Additionally, the balloon filling port would inflate the balloon—even while located in a patient—with air, fluid, or any other medium used by the skilled artisan.

According to yet another aspect of the present disclosure, the balloon is directly attached or operatively connected to the longitudinally extending tube distal end. The operative connection would run along the entire perimeter of one end of the longitudinally extending tube. However, the operative connection could also be along a distance or circumference less than the perimeter, so long as the balloon can be inflated by the longitudinally extending tube. In addition, the balloon may be fabricated from any material deemed suitable by a skilled artisan. Also, the balloon may be expanded to directly engage the interior walls of the alimentary canal. The engagement would be sufficient to retain distal expansion during endoscopic colon surgery.

According to a further aspect of the present disclosure, the alimentary device would have multiple interchangeable configurations: a home position and an active position. For example, in the home position, the distal end of the longitudinally extending tube would be coterminous or adjacent with the distal end of the cylindrical assembly. According to certain aspects of the present disclosure, the home position would facilitate initial placement of the multi-working channel device in a patient immediately before an endoscopy, colonoscopy, or surgery.

According to yet another aspect of the disclosure, the multi-working channel device would include a stylet, which is any slender probe, thin wire, or any other similar instrument used by a skilled artisan. The stylet would be insertable within a catheter or channel to maintain rigidity or patency. In addition, the stylet could be solid or hollow. The stylet could be made of metal, plastic, polymeric material, a combination thereof, or any other material used by a skilled artisan. The stylet would comprise a proximal end and a distal end. The distal end of the stylet would be operatively connected to the balloon of the longitudinally extending tube. This operative connection provides greater selectiveness as to where a skilled artisan could place the balloon. In addition, the stylet guides the balloon to a different placement during surgery if needed.

According to a further aspect of the disclosure, the stylet is adjustable between the home position and the active position. In the home position, while still being operatively connected, the balloon is at least partially within the longitudinally extending tube.

Alternatively, in the active position, the balloon is deployed from the longitudinally extending tube. The stylet selectively urges the balloon to the active position, facilitating employment of the multi-working channel device during surgery. In addition, the balloon is selectively inflated through the longitudinally extending tube to engage the walls within the interior of the alimentary canal.

According to yet another aspect of the invention, a method of using the multi-working channel device, wherein the method comprises the following order of steps: (i) inserting the multi-working channel device into a patient's alimentary canal, (ii) sliding the multi-working channel device to a desired position within the alimentary canal, (iii) sliding the stylet to a desired position within the alimentary canal, and (iv) selectively inflating the balloon through the longitudinally extending tube.

According to a further aspect of the invention, another method of using the multi-working channel device, wherein the method comprises the following order of steps: (i) inserting the multi-working channel device into a patient's alimentary canal, (ii) sliding the multi-working channel device to a desired position within the alimentary canal, (iii) selectively inflating the balloon through the longitudinally extending tube, and (iv) sliding the stylet to a desired position within the alimentary canal.

However, the skilled artisan would understand that additional obvious steps could be incorporated without departing from the teachings of the disclosed methods. One such step being partially inflating the balloon, utilizing the stylet, and then fully inflating the balloon. In addition, the disclosed methods could be used in a colonoscopy or an endoscopic colon surgery.

BRIEF DESCRIPTION OF THE SEVERAL VIEWS OF THE DRAWINGS

For a fuller understanding of the nature and advantages of the present method and process, reference should be had to the following detailed description taken in connection with the accompanying drawings, in which.

Figure 1:
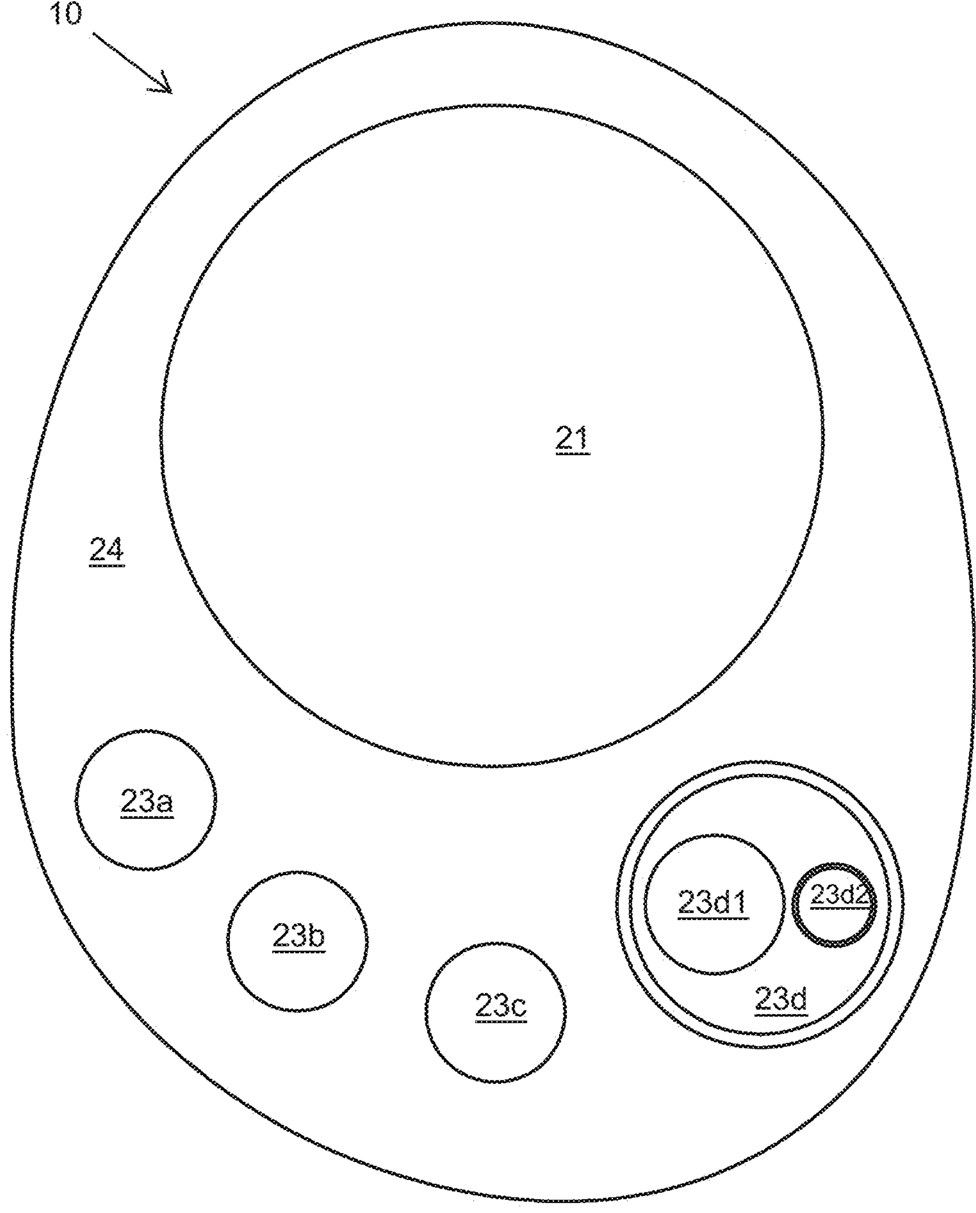
FIG. 1 illustrates a front cross-section of the multi-working channel device with balloon.

The drawings will be described in greater detail below.

DETAILED DESCRIPTION OF THE INVENTION

Reference is now made to the drawings wherein the showings are for purposes of illustrating aspects of the device only and not for purposes of limiting the same, and wherein like reference numerals are understood to refer to like components.

FIG. 1. shows a front cross-section view of the multi-working channel device (10) with a main channel (21) and a plurality of side working channels (23*a*, 23*b*, 23*c*, 23*d*). One side working channel (23*d*) also has two smaller side working channels (23*d*1, 23*d*2). The cylindrical assembly (20) has a distal end (24).

Figure 2:
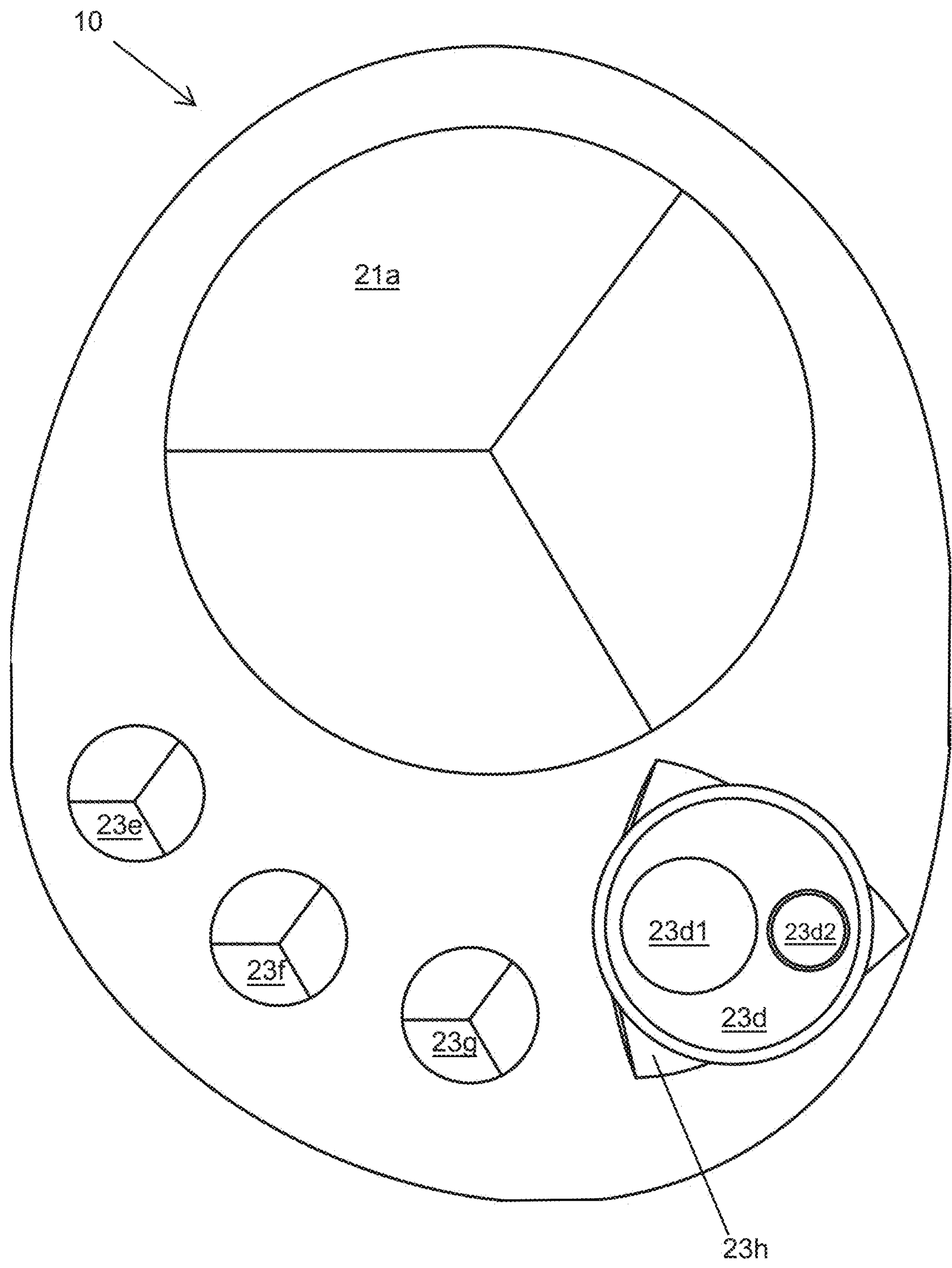
FIG. 2 illustrates a front view of the multi-working channel device with balloon.

FIG. 2. shows a front view of the multi-working channel device (10) with the main channel (21) covered by a flap (21*a*); in addition, the plurality of side working channels (23*a*, 23*b*, 23*c*, 23*d*) utilize flaps (23*e*, 23*f*, 23*g*, 23*h*). One side working channel (23*d*) has two smaller side working channels (23*d*1, 23*d*2).

Figure 3:
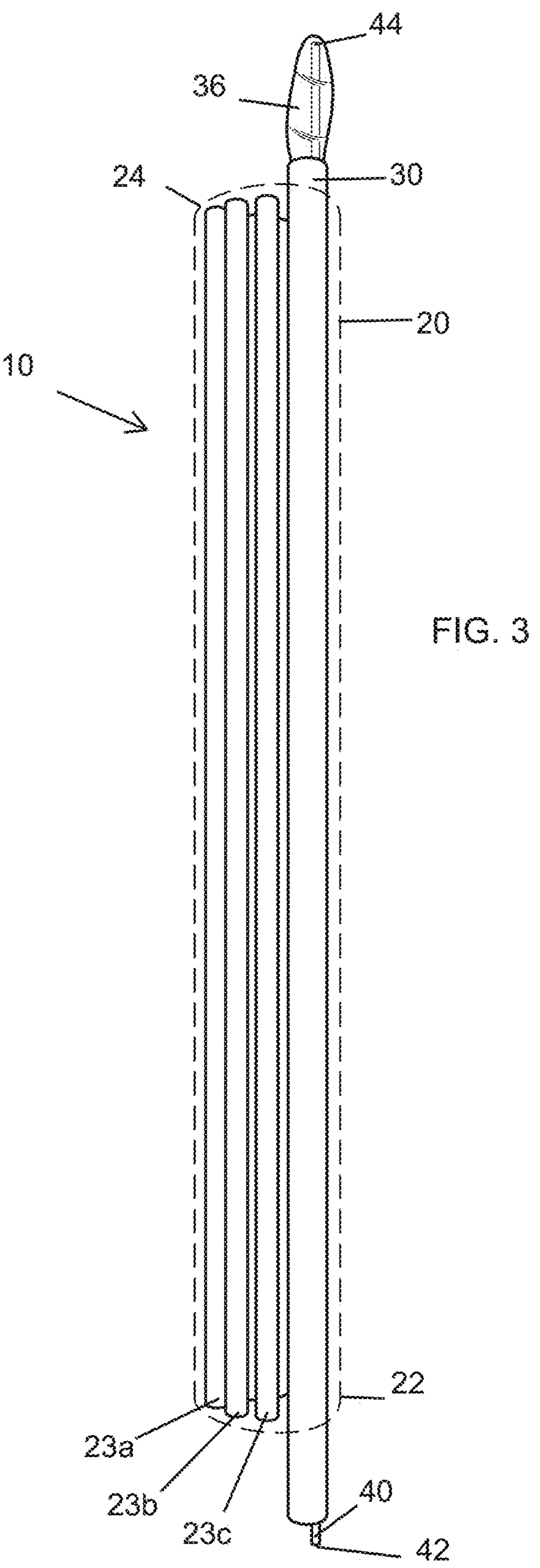
FIG. 3 illustrates a side phantom view of the multi-working channel device with balloon.

FIG. 3 shows a side phantom view of the multi-working channel device (10), with the plurality of side working channels (23*a*, 23*b*, 23*c*), with a cylindrical assembly (20). The cylindrical assembly (20) comprises a proximal end (22) and a distal end (24). The multi-working channel device (10) also comprises a stylet (40). The stylet (40) has a proximal end (42) and a distal end (44). The distal end (44) of the stylet (40) is operatively connected to the balloon (36). The balloon (36) can be inflated by a longitudinally extending tube (30) to retain distal expansion.

Figure 4:
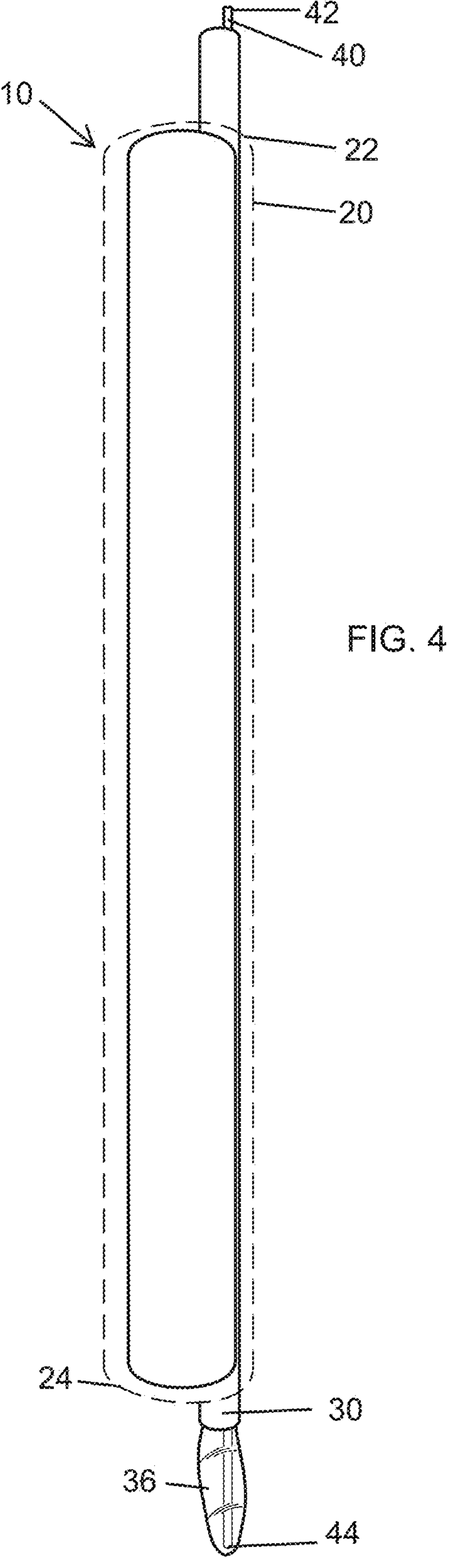
FIG. 4 illustrates another side phantom view of the multi-working channel device with balloon.

FIG. 4 shows another side view of the multi-working channel device (10) with a cylindrical assembly (20). The cylindrical assembly (20) comprises a proximal end (22) and a distal end (24). The multi-working channel device (10) also comprises a stylet (40). The stylet (40) has a proximal end (42) and a distal end (44). The distal end (44) of the stylet (40) is operatively connected to the balloon (36). The stylet (44) is housed in the longitudinally extending tube (30).

Figure 5:
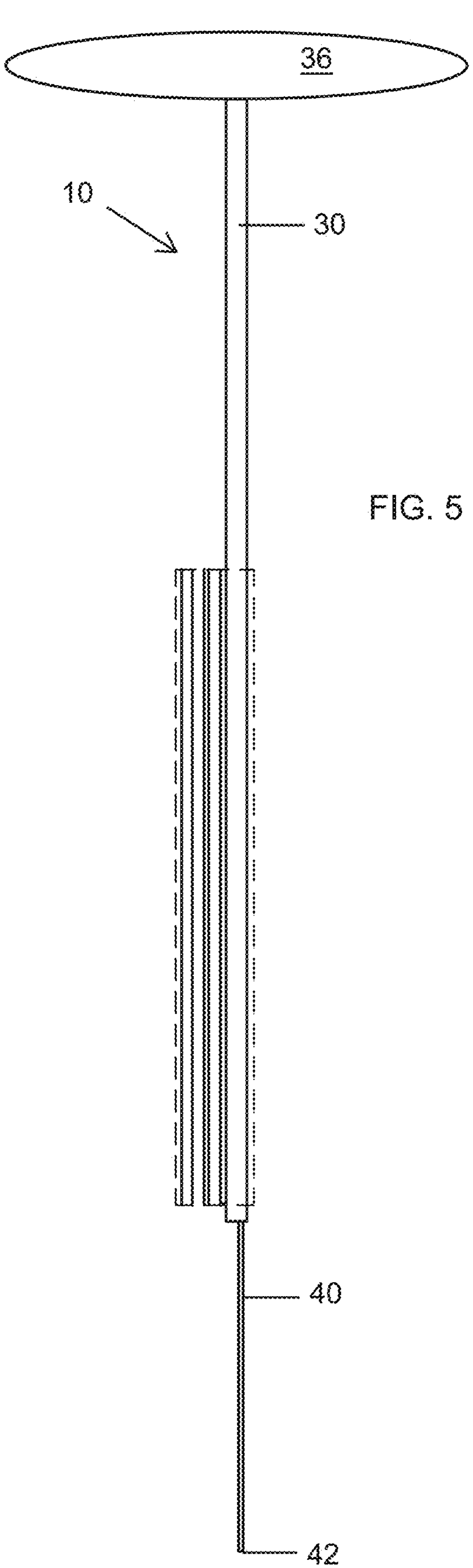
FIG. 5 illustrates yet another side phantom view of the multi-working channel device with balloon.

FIG. 5 shows yet another side phantom view of the multi-working channel device (10) with a cylindrical assembly (20). The multi-working channel device (10) comprises the stylet (40). The stylet (40) has a proximal end (42) and a distal end (44). The distal end (44) of the stylet (40) is operatively connected to the balloon (36). The balloon (36) is inflated by the longitudinally extending tube (30) to retain distal expansion.

Figure 6:
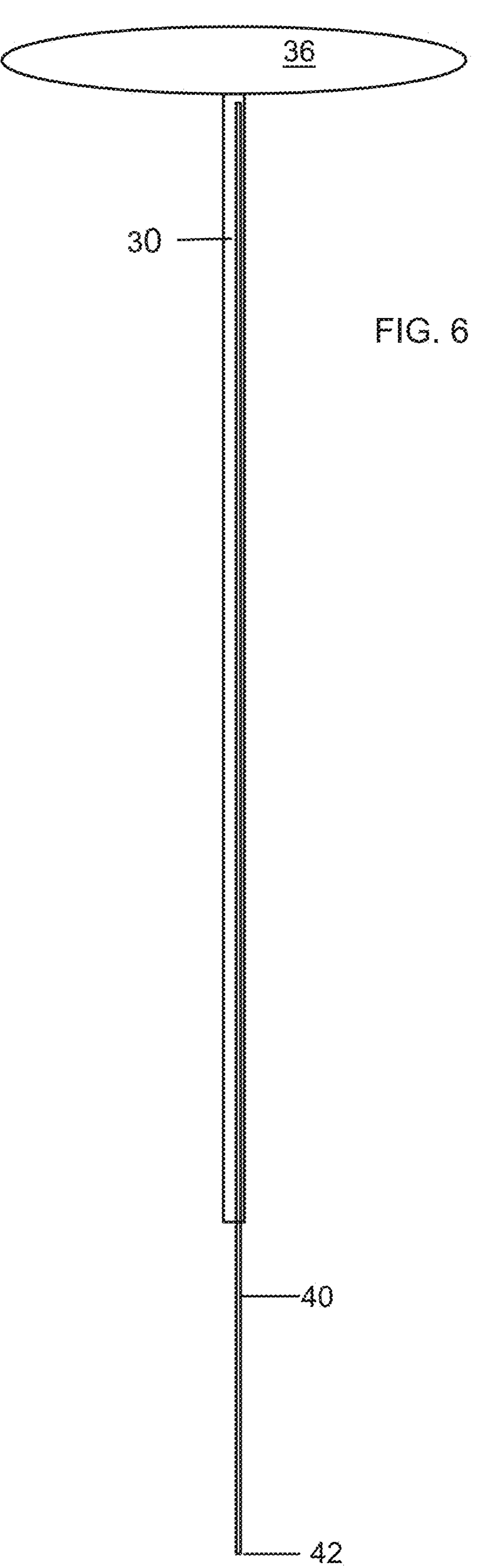
FIG. 6 illustrates a side view of the balloon, longitudinally extending tube, and stylet.

FIG. 6 shows a side view of the longitudinally extending tube (30) operatively connected to the balloon (36) while the balloon (36) is inflated. In addition, the stylet (40) is shown inside the longitudinally extending tube (30). While the balloon (36) is inflated, distal expansion is retained.

Figure 7:
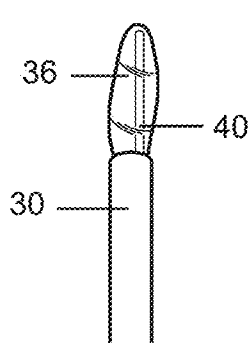
FIG. 7 illustrates another side view of the balloon, longitudinally extending tube, and stylet.

FIG. 7 shows another side view of the longitudinally extending tube (30) operatively connected to the balloon (36) while the balloon (36) is not inflated. In addition, the stylet (40) is shown inside the longitudinally extending tube (30). During employment of the multi-working channel device (10), the stylet (40) selectively urges the balloon (36) to the active position (60).

Figure 8:
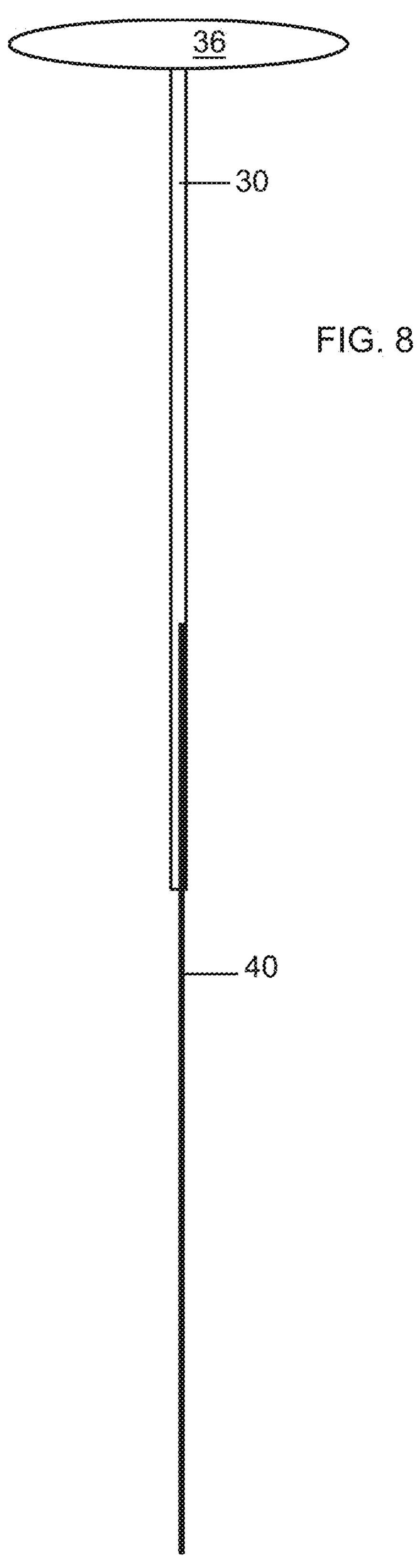
FIG. 8 illustrates another side view of the balloon, longitudinally extending tube, and stylet.

FIG. 8 shows a side view of the longitudinally extending tube (30) operatively connected to the balloon (36) while the balloon (36) is inflated. Once the balloon (36) is urged into the active position (60) by the stylet (40), the stylet (40) may be withdrawn to its home position (50). In addition, the balloon (36) is selectively inflated through the longitudinally extending tube (30). In addition, the stylet (40) is shown, while the stylet (40) is partially inside the longitudinally extending tube (30) and partially outside the longitudinally extending tube (30). While the balloon (36) is inflated, distal expansion is retained.

As depicted collectively in FIGS. 5, 6, 7, and 8, the stylet (40) can be adjusted between the home position (50) and the active position (60). In the home position (50), at least a portion of the balloon (36) is disposed within the longitudinally extending tube (30). In the active position (60), the balloon (36) is deployed from the longitudinally extending tube (30).

Figure 9:
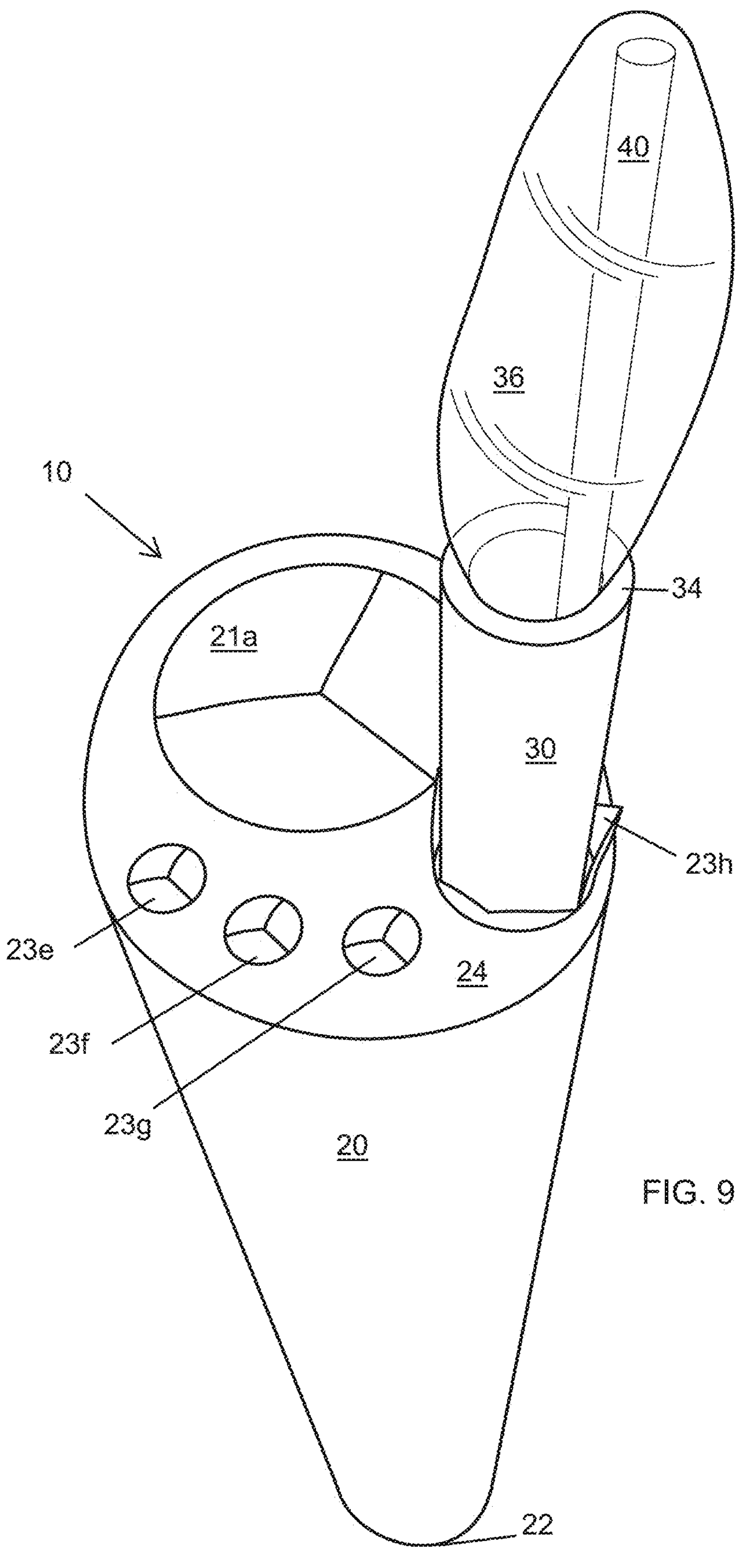
FIG. 9 illustrates a front isometric view of the multi-working channel device with balloon.

FIG. 9 shows a front isometric view of the multi-working channel device (10) comprising the main channel (21) and cylindrical assembly (20). The cylindrical assembly (20) comprises its distal end (24).

Also shown in FIG. 9, the multi-working channel device (10) also has a longitudinally extending tube (30), which comprises a proximal end (32), a distal end (34) able to be adjacent to the distal end (24) of the cylindrical assembly (20), and a balloon (36). The balloon (36) is operatively connected to the distal end (34) of the longitudinally extending tube (30).

Also provided in this disclosure is a method for using the multi-working channel device (10). This method includes the steps of: (i) inserting the multi-working channel device (10) into a patient's alimentary canal in a home position (50), (ii) sliding the multi-working channel device (10) to a desired position within the alimentary canal, (iii) sliding the stylet (40) to a desired position within the alimentary canal, and (iv) deploying the balloon (36) into an active position (60) by selectively inflating the balloon (36) through the longitudinally-extending tube (30).

While the apparatus, system, and method have been described with reference to various embodiments, those skilled in the art will understand that various changes may be made, and equivalents may be substituted for elements thereof, without departing from the scope and essence of the disclosure. In addition, many modifications may be made to adapt a particular situation or material in accordance with the teachings of the disclosure without departing from the essential scope thereof.

Therefore, it is intended that the disclosure is not limited to the embodiments disclosed, but that the disclosure will include all embodiments falling within the scope of the appended claims. In this application, all units are in the metric system and all amounts and percentages are by weight, unless otherwise expressly indicated. Also, all citations referred to herein are expressly incorporated herein by reference.

The invention claimed is:

1. A multi-working channel device (10) for balloon assisted containment of insufflated robotic/endoscopic operative fields, the multi-working channel device comprising:

a. a cylindrical assembly (20) comprising:
   i. a proximal end (22),
   ii. a distal end (24),
   iii. an interior space (26),
   iv. an aperture (28),
b. a longitudinally extending tube (30) comprising:
   i. a proximal end (32),
   ii. a distal end (34) coterminous with the distal end of the cylindrical assembly, and
   iii. a balloon (36) operatively connected to the longitudinally extending tube distal end, and
c. a stylet (40) having a proximal end (42) and a distal end (44), wherein the distal end of the stylet is operatively connected to the balloon, whereby the stylet can be adjusted between a home position (50), wherein the balloon is at least partially within the longitudinally extending tube, and an active position (60), wherein the balloon is deployed from the longitudinally extending tube, whereby the stylet selectively urges the balloon to the active position, the stylet being housed in the longitudinally extending tube and withdrawable toward the home position after the balloon is urged into the active position, whereby the balloon is selectively inflated through the longitudinally extending tube.

2. The multi-working channel device of claim 1, wherein the balloon is operatively connected along the entire circumference of the distal end of the longitudinally extending tube.

3. The multi-working channel device of claim 1, wherein the longitudinally extending tube further comprises an auxiliary tube and a balloon filling port.

4. The multi-working channel device of claim 1, wherein the balloon is filled with air.

5. The multi-working channel device of claim 1, wherein the balloon is filled with fluid.

6. A method of using the multi-working channel device of claim 1, wherein the method comprises the following order of steps:

i. inserting the multi-working channel device into a patient's alimentary canal, ii. sliding the multi-working channel device to a desired position within the alimentary canal, iii. sliding the stylet to a desired position within the alimentary canal, and iv. selectively inflating the balloon through the longitudinally extending tube.

7. The method of using the multi-working channel device of claim 6, wherein the method is used for a colonoscopy.

8. The method of using the multi-working channel device of claim 6, wherein the method is used for an endoscopy.

9. A multi-working channel device (10) for balloon assisted containment of insufflated robotic/endoscopic operative fields, the multi-working channel device comprising:

a. a cylindrical assembly (20) comprising:

i. a proximal end (22), ii. a distal end (24), iii. an interior space (26), iv. an aperture (28), b. a longitudinally extending tube (30) comprising:

i. a proximal end (32), ii. a distal end (34) adjacent with the distal end of the cylindrical assembly, and iii. a balloon (36) operatively connected to the longitudinally extending tube distal end, and c. a stylet (40) having a proximal end (42) and a distal end (44), wherein the distal end of the stylet is operatively connected to the balloon, whereby the stylet can be adjusted between a home position (50), wherein the balloon is at least partially within the longitudinally extending tube, and an active position (60), wherein the balloon is deployed from the longitudinally extending tube, whereby the stylet selectively urges the balloon to the active position, the stylet being housed within the longitudinally extending tube and withdrawable after deployment of the balloon, whereby the balloon is selectively inflated through the longitudinally extending tube.

10. The multi-working channel device of claim 9, wherein the balloon is operatively connected along the entire circumference of the distal end of the longitudinally extending tube.

11. The multi-working channel device of claim 9, wherein the longitudinally extending tube further comprises an auxiliary tube and a balloon filling port.

12. The multi-working channel device of claim 9, wherein the balloon is filled with air.

13. The multi-working channel device of claim 9, wherein the balloon is filled with fluid.

14. A method of using the multi-working channel device of claim 9, wherein the method comprises the following order of steps:

i. inserting the multi-working channel device into a patient's alimentary canal, ii. sliding the multi-working channel device to a desired position within the alimentary canal, iii. sliding the stylet to a desired position within the alimentary canal, and iv. selectively inflating the balloon through the longitudinally extending tube.

15. The method of using the multi-working channel device of claim 14, wherein the method is used for a colonoscopy.

16. The method of using the multi-working channel device of claim 14, wherein the method is used for an endoscopy.

17. The method of using the multi-working channel device of claim 14, wherein the method is used for endoscopic colon surgery.

18. A multi-working channel device (10) for balloon assisted containment of insufflated robotic/endoscopic operative fields, the multi-working channel device comprising:

a. a cylindrical assembly (20) comprising:

i. a main channel (21), ii. a proximal end (22), iii. a plurality of side-working channels (23), iv. a distal end (24), v. an interior space (26), vi. an aperture (28), b. a longitudinally extending tube (30) comprising:

i. a proximal end (32)

ii. a distal end (34) coterminous with the distal end of the cylindrical assembly, and iii. a balloon (36) operatively connected to the longitudinally extending tube distal end, and c. a stylet (40) having a proximal end (42) and a distal end (44), wherein the distal end of the stylet is operatively connected to the balloon, whereby the stylet can be adjusted between a home position (50), wherein the balloon is at least partially within the longitudinally extending tube, and an active position (60), wherein the balloon is deployed from the longitudinally extending tube, whereby the stylet selectively urges the balloon to the active position, the stylet being partially withdrawable after deployment while the balloon remains selectively inflatable through the longitudinally extending tube, whereby the balloon is selectively inflated through the longitudinally extending tube.

19. The multi-working channel device of claim 18, wherein the balloon is operatively connected along the entire circumference of the distal end of the longitudinally extending tube.

20. The multi-working channel device of claim 18, wherein the longitudinally extending tube further comprises an auxiliary tube and a balloon filling port.

* * * * *